United States Patent [19]

Freese

[11] 4,261,367
[45] Apr. 14, 1981

[54] APPARATUS FOR MEASURING THE AXIAL LENGTH OF AN EYE

[75] Inventor: Manfred Freese, Thornhill, Canada

[73] Assignee: Radionics Limited, Montreal, Canada

[21] Appl. No.: 88,130

[22] Filed: Oct. 25, 1979

[51] Int. Cl.³ .............................................. A61B 10/00
[52] U.S. Cl. .................................... 128/660; 73/611; 73/616
[58] Field of Search ............................. 128/660–663; 73/611–618

[56] References Cited

U.S. PATENT DOCUMENTS

| 3,821,891 | 7/1974 | Collins et al. | 128/660 |
| 3,872,858 | 3/1975 | Hudson et al. | 128/660 |

OTHER PUBLICATIONS

Mortimec, A. J. et al., "A Simple Digital Echo Oculometer", DIG. of the 11th Intnl. Conf. on Medical & Biol. Engrg., Ottawa 1976, pp. 508–509.
Mortimer, A. J. et al., "An Instrument for Ultrasonic Biometry", Canadian Jrnl. Opthalmology, Vol. 12, 1977, pp. 318–320.
Leary, G. A., "Basic Techniques for Applying Ultrasonics to Opthalmic Diagnosis and Measurement".

Primary Examiner—Robert W. Michell
Assistant Examiner—Francis J. Jaworski
Attorney, Agent, or Firm—Fleit & Jacobson

[57] ABSTRACT

An apparatus for measuring the axial length of the eye is disclosed. The apparatus comprises circuitry for transmitting repetition ultrasonic pulses along the ocular axis of the eye and for receiving echo pulses reflected from the retina of the eye. The reflected echo pulses are then amplified. Gate circuits receive the amplified signals and pass logic signals triggered by retinal echo pulses exceeding predetermined thresholds. A digital counter displays the axial length of the eye as a function of a distance travelled by the retinal echo pulses. A time slot is generated during which echo pulses originating from the posterior wall of the eye can be received, and an echo triggered gate width generator enables the passage of logic signals triggered by retinal echo pulses exceeding a threshold in the generated time slot. The echo-triggered gate width generations also connected to a latching circuit, thereby preventing mistriggering of the echo triggered gate width generator by echoes originating from structures behind the retina.

8 Claims, 3 Drawing Figures

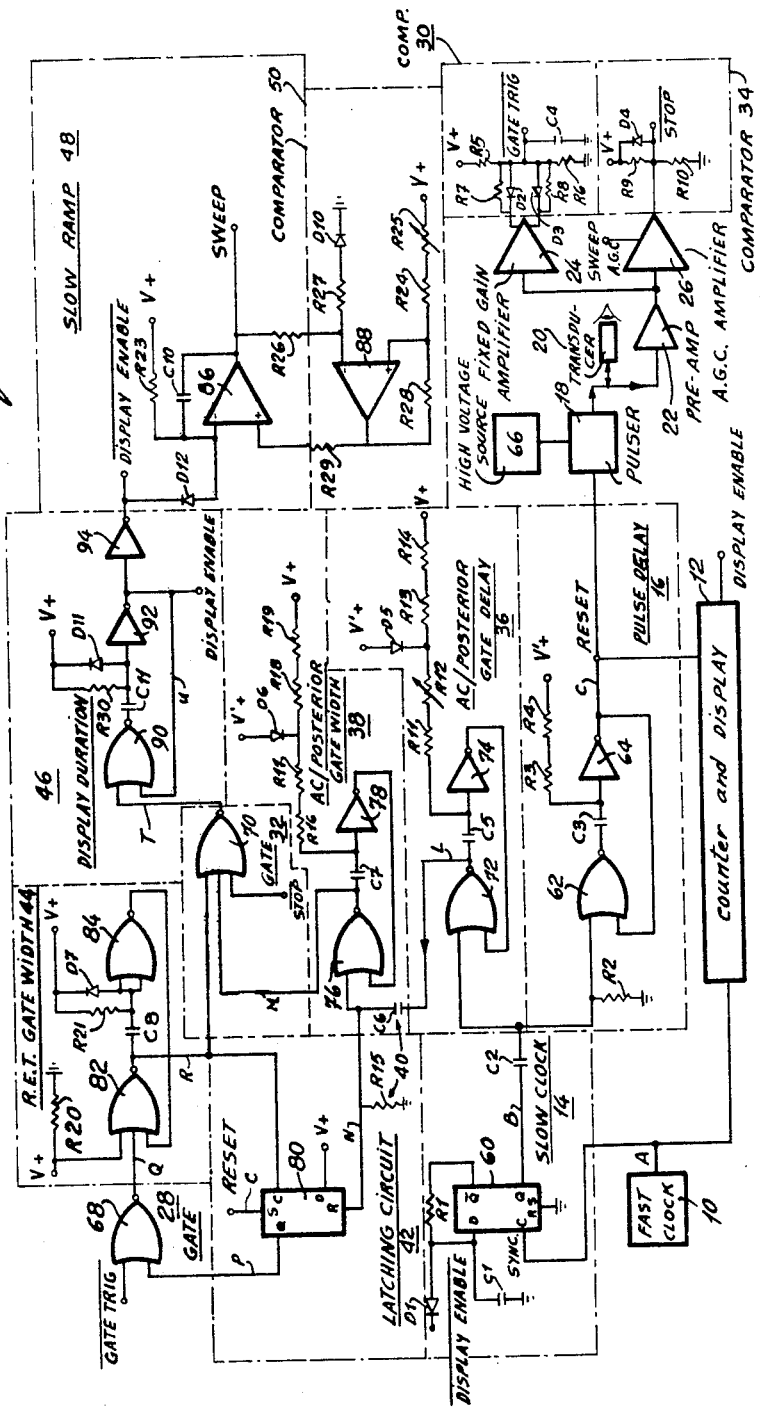

APPARATUS FOR MEASURING THE AXIAL LENGTH OF AN EYE

This invention relates to an apparatus for effecting rapid and accurate ultrasonic measurements of the axial length of the eye.

A compact and simple ultrasonic instrument (echo-oculometer) for measuring the axial length and anterior chamber depth of the eye has been described in the literature by Mortimer et al. in the Proceedings of the 11th Intl. Conf. on Medical and Biol. Engng. 1976 pp. 508–509 and by Mortimer et al. in the Canadian J. Ophthal. Volume 12, 1977 pp. 318–320.

Advantages of this instrument over conventional A-Scan devices employing cathode ray tubes for display are that a display of the A-Scan is not essential, the results are immediately available on a counter and are expressed in convenient numerical units.

The above echo-oculometer utilizes techniques similar to those used in the echo-encephalograph invented by Hudson et al. and described in U.S. Pat. No. 3,872,858 issued Mar. 25, 1975 and its corresponding Canadian Pat. No. 973,632 issued Aug. 26, 1975. The echo-oculometer employs a transducer which emits a short pulse of ultrasound aimed along the ocular axis. The echoes returning from the various surfaces within the eye are received by the same transducer and the time required for the sound pulse to return is converted to a length measurement. Two range gates consisting of electronic logic circuits allow echoes from particular interfaces to be selected and the corresponding time interval to be measured. The retinal echo is selected for the axial length and the anterior lens echo is selected for the anterior chamber depth measurement. The statistical accuracy of the determinations may be increased by averaging several readings.

Three important features of the above echo-oculometer device are that it employs a slow gain sweep, a crystal controlled time base of a particular frequency, and a special delay circuit which determines the time at which the counter starts to count.

In contrast to the echo-encephalograph which employs a second fast gain sweep (funcioning analogously to the time varied gain or TGC of the conventional A and B scan equipment), the oculometer has only a slow gain sweep since compensation for tissue attenuation is not needed. For the slow gain sweep, the gain does not vary significantly during the time a given pulse is transmitted and its echoes are received. Rather the receiver gain increases from a transmitted pulse to the next until the range-gated signal exceeds a predetermined threshold, stoping the counter (displaying the accumulated count), or until the maximum receiver gain level is reached whereupon the measurement cycle is automatically repeated.

The gain sweep has two functions. It is supposed to compensate for differences in the amplitudes of the received echoes (in different eyes) and, more important, it is supposed to insure that the strongest echo detected in the range gate interval selected will be the first to exceed the detection threshold thereby stopping the counter.

Key assumptions made in the operation of the above echo-oculometer device are that (1) when the beam is directed along the axis of the eye, the first echo in the selected range gate will be the largest echo, and (2) if the beam is directed off-axis, the echoes received will be too weak (due to the inclination of the reflecting interface and the transducer directivity) to exceed the range gate detection threshold.

While these assumptions are generally true for the anterior lens echoes (anterior chamber depth), research and clinical experience conclusively show that this is not always true for the much more important retinal echoes (axial length). In a significant number of cases, other interfaces and structures behind the retina give rise to the largest echoes. This can result in errors in the axial length determinations of as much as 3 mm which corresponds to an error in the lens power determinations of about 8 or 9 diopters. An eror of this magnitude is altogether unacceptable. Furthermore, it must be emphasized that although this problem is much more common for the case of off-axis beam incidence, it will still sometimes occur when the beam is properly aligned.

Finally, if readings are taken with the beam improperly aligned, the accuracy of the axial length determinations will be decreased either due to the problem just described or in the case where the retinal echo does stop the counter, the fact that a chord shorter than the axial diameter is being measured.

One method of counteracting these problems would be to increase the beam directivity but this is subject to both theoretical and practical limitations. Another approach might be to lower the upper limit of the swept gain. However, there are obvious constraints since the instrument must accommodate a considerable range of ultrasonic and geometrical characteristics for different eyes.

Aother method would be to require the presence of the anterior and posterior lens echoes (either one but preferably both) of a magnitude equal or greater than some specified fraction of the retinal echo threshold (typically ½ or more) as a necessary condition for a valid reading. In fact, the standard A-scan technique (used in determining the axial length) consists of insuring that both the anterior and posterior lens echoes are simultaneously present together with the retinal echo, and then maximizing the two lens echoes while maintaining a good clean and large retinal echo. The technique is illustrated in detail by Leary in Ultrasonics April 1967, pp. 84–87. Under normal conditions, the symmetry of the eye is such that following the above procedure will insure good axial alignment.

Implementing the above lens echo conditions in the form of electronic circuits to assure that readings are obtained only under conditions of good alignment is straightforward and is obvious to those skilled in the art. However, while this would greatly reduce the likelihood of incorrect triggering by structures behind the retina, it does not entirely eliminate the problem. Also the difficulty of achieving exact alignment without reference to an A-Scan can make the actual obtaining of readings very problematic. Certainly adding the lens echo condition reduces the speed with which valid readings can be obtained. This is an important consideration when dealing with older or uncooperative patients.

It is therefore the object of the present invention to provide an apparatus for effecting rapid and accurate ultrasonic measurements of the axial length of the eye.

The apparatus, in accordance with the invention, comprises a transducer adapted to transmit repetitive ultrasonic pulses along the ocular axis of the eye of a patient and receive echo pulses reflected from the retina of the eye, a fixed gain amplifier connected to the transducer for amplifying such reflected echo pulses, an automatic gain controlled amplifier also connected to the transducer for amplifying the reflected echo pulses, control means coupled to the automatic gain controlled amplifier for gradually increasing the gain of the amplifier during a measurement cycle, first and second gate circuits controlled by the output of the fixed and automatic gain controlled amplifier, respectively, and adapted to pass logic signals triggered by retinal echo pulses exceeding first and second predetermined thresholds, a digital counter connected to the second gate circuit and adapted to display the axial length of the eye as a function of the distance travelled by the retinal echo pulses, a gate delay initiated by a slow clock, a gate width generator connected to the gate delay for generating a time slot during which echo pulses originating from the posterior wall of the eye can be received, a latching circuit responsive to the gate delay for enabling the first gate circuit to pass logic signals triggered by echo pulses exceeding the first threshold, a retinal echo triggered gate width generator interconnecting the first and second gate circuits and responsive to the first gate circuit for enabling the second gate circuit to pass logic singals triggered by retinal echo pulses exceeding the second threshold in the time slot generated by the gate width generator, the output of the retinal echo triggered gate width generator being also connected to the latchng circit for blocking the first gate circuit immediately after receipt of the first logic signal triggered by a retinal echo pulse, thereby preventing mistriggering of the retinal echo triggered gate width generator by echoes originating from structures behind the retina.

The above control means includes a slow ramp generator adapted to generate a ramp voltage which is applied to the automatic gain controlled amplifier in such a manner that the gain of the amplifier varies from a minimum at the start of the measurement cycle to a preset maximum after a number of cycles.

A pulser is connected to the transducer for applying sharp high voltage spikes to such transducer to shock excite it so as to direct an ultrasonic pulse into the eye being examined. The pulser is triggered by the slow clock. A fast clock, operating at a frequency in MHz which is ½ times the average velocity of ultrasound in the eye expressed in units of 0.1 mm per microsecond, provides the counter times base and is used to synchronize the slow clock.

A pulser delay is located between the slow clock and the pulser to insure that the counter starts counting at the correct time.

The invention will now be disclosed, by way of example, with reference to the accompanying drawings in which:

FIG. 3 is a circuit diagram of the echo-oculometer constructed according to the prsent invention.

Figure 1:
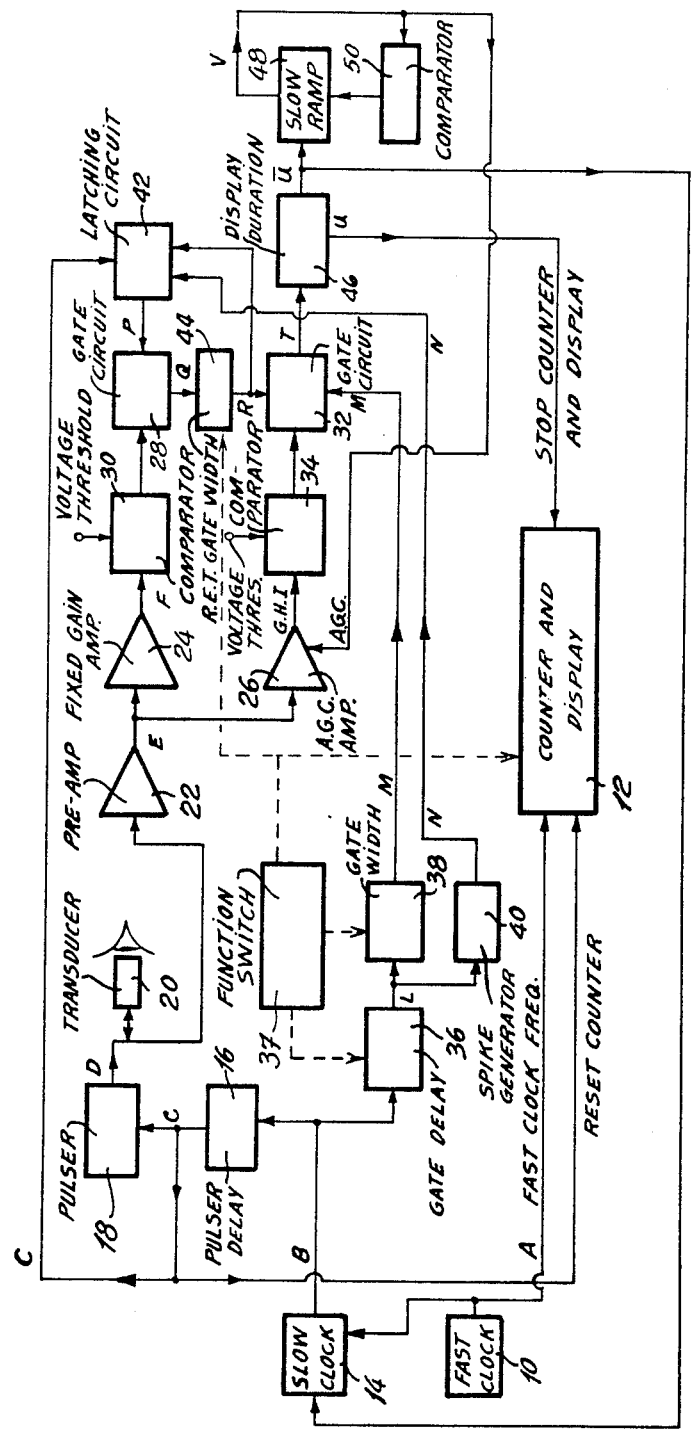
FIG. 1 is a block diagram of an exemplary embodiment of the invention.
Figure 2:
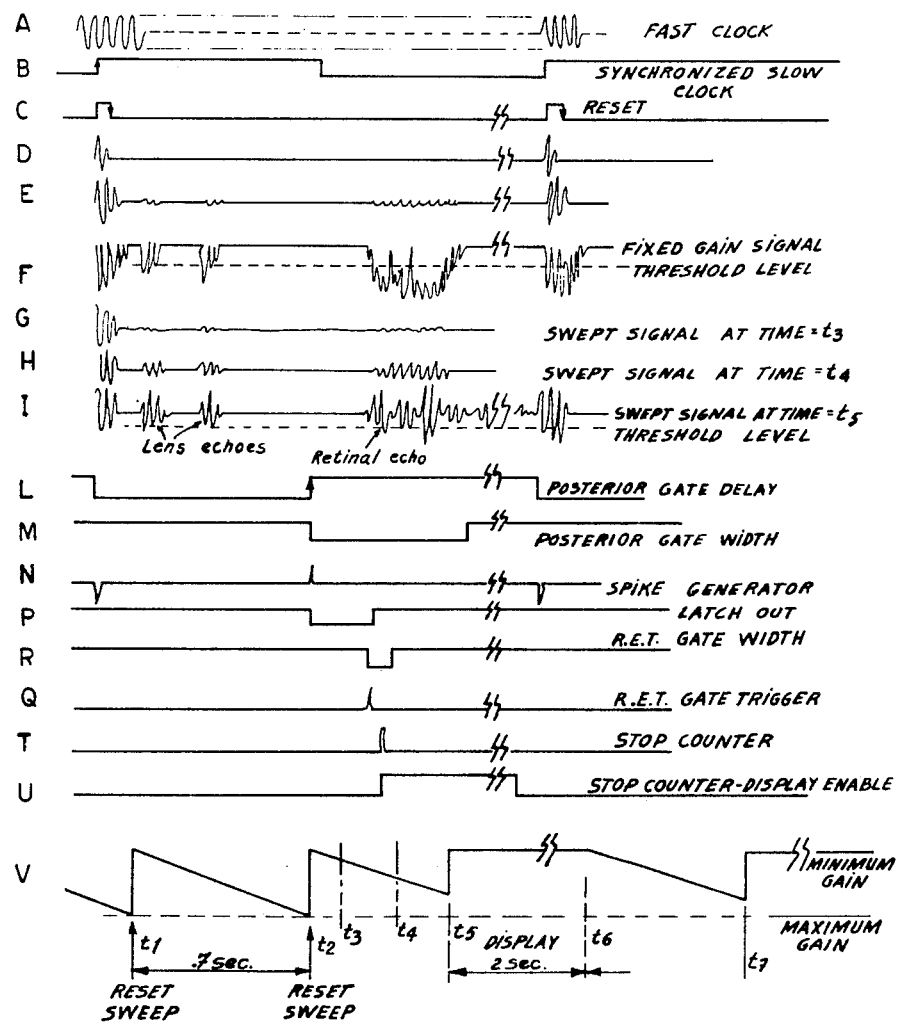
FIG. 2 is a series of waveforms produced at various points in the block diagram of FIG. 1.

Referring to FIGS. 1 and 2, there is shown a fast clock 10 which generates a continuous signal at a frequency in MHz which is numerically equal to ½ times the average velocity of ultrasound in the eye (1553 m/sec) in units of 0.1 mm per microsecond, that is 7.765 MHz, and has a sinusoidal waveform as illustrated at A in FIG. 2. The clock 10 feeds a signal to a counter-display 12 and to a slow clock 14. The slow clock 14 generates a square wave at a frequency of about 60 Hz as shown at B in FIG. 2 of the drawings. The operation of the slow clock 14 is synchronized to the fast clock 10. The output signal of the slow clock is applied to a pulser delay 16 which generates a repetitive pulse signal such as shown at C in FIG. 2. The pulser delay 16 triggers a pulser 18 on the positive going edge of the waveform C and at the same time resets the counter 12. The counter begins counting on the negative going edge of the waveform C to compensate for the propagation time of the ultrasonic pulse from the transducer to the eye and from the eye to the transducer. Pulser 18 generates a sharp high voltage spike, such as shown at D in FIG. 2, whish is used to shock excite a transducer 20 to direct an ultrasonic pulse through the eye being examined. This pulse travels through the eye and is reflected by the various surfaces and returned to the transducer. These echo pulses are picked up by the transducer and converted back to electrical signals which are directed to a preamplifier 22 providing an output such as shown at E in FIG. 2. The output of the preamplifier 22 is applied to a fixed gain amplifier 24 providing an amplified output such as shown at F in FIG. 2 and to an automatic gain control amplifier 26 providing an amplified output such as shown at G, H or I in FIG. 2 depending on the gain of the amplifier as controlled by the voltage V applied to its automatic gain control terminal. The output of the fixed gain amplifier 24 is fed to a first gate circuit 28 through a comparator 30 which sets a signal threshold level for the output of amplifier 24 as illustrated by a dashed line through waveform F in FIG. 2. Similarly, the output of the automatic gain control amplifier 26 is fed to a second gate circuit 32 through a comparator 34 which sets a signal threshold level for the output of amplifier 26 as illustrated by a dashed line through waveform I in FIG. 2.

The present apparatus is capable of measuring not only the axial length (AL) of an eye by detecting the retinal echo pulses but also and anterior chamber (AC) depth by detecting the anterior lens echo pulses. As mentioned previously, the measurement of the anterior lens echoes is not the object of the present invention, therefore the portion of the circuitry which is concerned with the measurement of the retinal lens echo will be primarily disclosed. In order to permit gate circuits 28 and 32 to pass logic signals triggered by the echo pulses which are reflected from the desired surfaces of the eye, there is provided a gate delay 36 which is triggered by the positive leading edge of the signal B appearing at the output of the slow clock 14. Gate delay 36 provides an output waveform such as illustrated at L in FIG. 2, and triggers the gate width generator 38 on the positive edge of the waveform L. If the anterior chamber depth was to be measured, the delay would of course be much shorter so as to allow gating of the echo pulses originating from the anterior lens surface of the eye. A function switch 37 is provided for selecting which one of the measurements is to be performed by the apparatus. The gate width generator 38 generates a signal M as shown in FIG. 2. Signal M is fed to gate 32 and controls the time slot during which gate 32 is opened. Gate width generator 38 is also responsive to function switch 37 for selection of the desired measurement to be performed. The output L of gate delay 36 is also applied to a spike generator 40 which generates a signal shown at N in FIG. 2. Signal N is fed to a latching circuit 42 which generates a signal P, as shown in FIG.

2, for controlling the opening of gate circuit 28. Latching circuit 42 is reset by the output C of the pulser delay at the beginning of each cycle.

A retinal echo triggered gate width generator 44 is connected between gates 28 and 32 and is triggered by output signal Q of gate circuit 28 when a retinal echo signal exceeding the threshold of comparator 30 is present. The retinal echo triggered gate width generator 44 provides an output R, as shown in FIG. 2, which is applied to the gate circuit 32 to permit the gate to pass logic signals triggered by echo signals originating from automatic gain control amplifier 26 exceeding the threshold of comparator 34. The output R is also fed to the latching circuit 42 to cause the latching circuit to immediately disable gate circuit 28 after receipt of the first logic signal triggered by an echo signal originating from the fixed gain amplifier 24. Thus, gate circuit 28 is latched out immediately after the retinal echo pulses are detected to prevent retriggering of 44 thereby preventing gate 32 from passing logic signals triggered by echo pulses originating from structures behind the retina. The retinal echo triggered gate width generator 44 is disabled by the function switch 37 during anterior chamber measurement because it is not required.

The output T of gate 32 is fed to a display duration circuit 46 which provides an output U to stop the counter and display, for a few seconds, the distance travelled by the retinal echo pulse as an indication of the axial length of the eye.

The gain of the fixed gain amplifier 24 is set by an amount approximately 10 to 14 dB greater (3 to 5 times greater) than the maximum gain of the automatic gain control amplifier 26. This insures that the retinal echo signal will be of sufficient amplitude to exceed the threshold of the comparator 30 and that the retinal echo triggered gate width generator 44 will not be mistriggered by an echo pulse of greater amplitude originating from structures behind the retina.

The gain of the automatic gain control amplifier 26 is varied by a slow ramp generator 48 which generates a voltage of increasing negative amplitude V starting from a minimum value at the beginning of the measurement up to a maximum value set by a comparator 50. The output $\overline{U}$ of the display duration circuit 46 is applied to the slow clock to enable the same, and to the slow ramp generator 48 to reset the slow ramp generator voltage V to its minimum value, when the automatic gain control amplifier 26 has sufficient gain to pass the signals exceeding the threshold set by comparator 34.

The invention will now be disclosed with reference to the more detailed circuit diagram of FIG. 3 which is intended to give a better understanding of the invention but not to limit the scope thereof. The non-detailed blocks as well as the circuit diagrams outlined in FIG. 3 by broken lines carry the same references as the corresponding blocks of FIG. 1.

The fast clock 10 is a conventional crystal controlled oscillator operating at a frequency of 7.765 MHz as mentioned previously. The output A of the fast clock is fed to the counter-display 12 which is a conventional digital counter capable of displaying a count when energized to do so. A suitable example of such a counter is RCA No. ICAN-6733. The counter-display is therefore operated by the fast clock to indicate directly the axial length of the eye. For synchronizing of the clocks, the output A of the fast clock is also applied to the clock input C of a conventional type D flip-flop 60 which acts as a slow clock. The timing period of the slow clock is about 60 Hz as mentioned previously and is determined by a resistor R1 connected between terminals D and $\overline{Q}$ of the flip-flop and capacitor C1 connected between terminal D and ground. Flip-flop 60 may be enabled by clamping terminal D through diode D1 as will be disclosed later.

The output of the slow clock is applied to pulser delay 16 through coupling capacitor C2 and resistor R2. The pulser delay is comprised of a CMOS NOR gate 62 and an inverter 64. Gate 62 has a first input connected to the slow clock and a second input connected to the output of inverter 64. The output of gate 62 is connected to the input of the inverter 64 through capacitor C3. A positive potential V'+ is also applied to the input of the inverter through resistors R3 and R4. Gate 62 and inverter 64 form a well known monostable circuit. The output of the pulser delay is as shown at C in FIG. 2 of the drawings.

The pulser 18, which is energized from a conventional high voltage source 66, is triggered on the rising edge of output C of the pulser delay and produces a sharp high voltage spike D which is used to shock excite the transducer 20 to direct an ultrasonic pulse into the eye of the person being examined. This pulse travels through the eye and is reflected by various surfaces of the eye, as mentioned previously, and returns to the transducer. The echo pulses are detected by the transducer 20 and converted back to electric signals which are fed to preamplifier 22. The output of preamplifier 22 is applied to a fixed hi-gain amplifier 24 and to an automatic gain control amplifier 26. The above mentioned circuit elements 18, 22, 24 and 26 are conventional and need not be disclosed in detail.

The output F of fixed hi-gain amplifier 24 is full-wave rectified by diodes D2 and D3 and clamped to the voltage level determined by the voltage divider resistors R5, R6 connected across a source V+. The clamped signal ($\overline{\text{Gate trig}}$) is fed to one of the inputs of a two input NOR gate 68. The echo signal detection threshold voltage is equal to the difference between the NOR gate logic threshold and the above clamping voltage. In this particular embodiment, therefore, the resistor network R5 and R6 and the logic threshold (approximately ½V+ for CMOS logic) constitute essentially the equivalent of the comparator 30 while the NOR gate 68 constitutes the gating circuit 28.

Resistors R7 and R8 and capacitor C4 provide low-pass filtering for the echo signals which improves the detection performance. While not essential, full-wave rectification of the signal simplifies low-pass filtering of the signal (in order to improve the signal to noise ratio).

In a manner similar to the preceeding, the output (G, H, I) of the automatic gain control amplifier 26 is clamped to the voltage level determined by the voltage divider, resistors R9 and R10, connected across the V+ source. The clamped signal ($\overline{\text{stop}}$) is fed to one input of the NOR gate circuit 70. R9 and R10 and the NOR gate logic threshold thus form the equivalent of the comparator 34, and the three input NOR gate 70 corresponds to the gating circuit 32.

The gain of the amplifier 26 is variable and depends on the "sweep" voltage applied to its AGC terminal as will be disclosed later.

A diode D4 is connected across the resistor R9 to protect the CMOS against overvoltage.

The output B of the slow clock 14 is also applied to the gate delay 36. Gate delay 36 comprises a CMOS NOR gate 72 and an inverter 74 which are interconnected in the same manner as in pulser delay 16 to form a monostable. Gate 72 has a first input connected to the slow clock 14 and a second input connected to the output of inverter 74. The output of gate 72 is connected to the input of the inverter 74 through a capacitor C5. A positive potential V+ is also applied to the input of the inverter through resistors R11–R14. The time constant of the monostable is controlled by resistors R11–R14 and capacitor C5. The output L of the monostable is as shown in FIG. 2 of the drawings. Gate delay 36 may also be used for anterior chamber measurement and, in such a case, the time constant of the R-C circuit may be changed by clamping the connecting point of resistors R12 and R13 to the voltage source V'+ through a diode D5. The clamping action is performed by operating a switch in function switch 37 (FIG. 1). As mentioned previously, the purpose of the gate delay 36 is to delay the operation of the gate width generator 38 which sets the time slot during which the desired echo is to be detected.

The output L of the gate delay 36 is applied, through a capacitor C6, to the gate width generator 38 which comprises a CMOS NOR gate 76 and an inverter 78. The gate width generator is a monostable of the same type as the one of the pulser delay 16 and the gate delay 36. The first input of the gate 76 is connected to output L of the gate delay and its second input is connected to the output of inverter 78. The output of gate 76 is connected to the input of inverter 78 through a capacitor C7. A positive potential source V+ is also connected to the input of inverter 78 through resistors R16–R19. The time constant of the monostable is set by resistors R16–R19 and capacitor C7. The output M of the monostable is as shown in FIG. 2 of the drawings.

The output M of the gate width monostable 38 determines the length of time during which the echo returned from the posterior part of the eye will be detected. Such output M is applied to the gate circuit 32 as will be disclosed later. The gate width generator 38 may also be used for anterior chamber measurement and, in such a case, the time constant of the R-C circuit will be changed by clamping the connecting point of resistors R17 and R18 to V'+ through a diode D6. This is performed by function switch 37.

The output L of the gate delay 36 is also applied to a latching circuit 42 through a spike generator 40 formed by resistor R15 and capacitor C6. In the embodiment disclosed, latching circuit 42 is a conventional type D flip-flop 80. The output N of the spike generator is applied to the reset terminal of flip-flop 80 to reset the output of the flip-flop to low at the beginning of the time slot during which the echoes returned from the posterior part of the eye are to be detected, as indicated by waveform P in FIG. 2 of the drawings.

The output P of the latching circuit is applied to the CMOS NOR gate 68 to enable the gate. When no echo signal (amplified by fixed gain amplifier 24) exceeds the threshold set by comparator 30, the output Q of gate 68 remains low.

CMOS NOR gates 68 and 70 are interconnected by a retinal echo triggered (R.E.T.) gate width generator 44 comprising a CMOS NOR gate 82 and an inverter 84 which operate as a monostable. Gate 82 has a first input connected to ground through resistor R20, a second input connected to the output Q of gate 68 and a third input connected to the output of inverter 84. The output of gate 82 is connected to the input of inverter 88 through capacitor C8. The input of the inverter 84 is also connected to a positive potential source V+ through resistor R21. The inverter is protected against overvoltage by diode D7. The input of the inverter is normally high as it is connected to V+ and its output low, so that when the output Q of gate 68 is low (no echo signal exceeding the threshold of comparator 30), the output R of gate 82 is high. However, when an echo signal exceeding the threshold level is received, the output Q of gate 68 turns high and the output R of gate 82 turns low. The output R of gate 82 is applied to terminal C (clear) of flip-flop 80 to turn output Q of the flip-flop high to immediately block gate 68 and so prevent the R.E.T. gate width generator from being retriggered after it has been triggered by a retinal echo signal. Thus, output Q is only a narrow spike such as shown in FIG. 2 of the drawings. After approximately one microsecond as set by resistor R21 and capacitor C8, the output of inverter 84 returns to low and the output of gate 82 to high thereby blocking gate 70. As a result, any subsequent echos which exceed the threshold of comparator 34 are prevented from triggering gate 32. If no retinal echo signal exceeding the threshold level of the comparator 30 is detected, flip-flop 80 is set (Q=1) by the output C of pulser delay 16 at the beginning of the next cycle to block gate 68 and to prevent the latching circuit 42 from being activated by echo signals detected in the gate delay interval which would disable the R.E.T. gate width generator 44 prematurely. The R.E.T. gate width generator 44 may also be disabled by applying a positive voltage V'+ to the first input of gate 82. This may be done by a switch of function switch 37 when making an anterior chamber measurement as the R.E.T. gate width generator is not needed for such an operation.

When a retinal echo pulse is detected, the output of the R.E.T. gate width generator is applied to the first input of the three input NOR gate 70. As long as the retinal echo signal amplified by the automatic gain control (AGC) amplifier does not exceed the threshold set by comparator 34, the clamped output signal $\overline{stop}$ applied to the third input of gate 70 is logically high and the output T of gates 70 is low.

As mentioned previously, the gain of the AGC amplifier 26 is controlled by a slow ramp generator 48 and a comparator 50. The slow ramp generator 42 is a conventional Miller integrator comprising a resistor-capacitor charging network consisting of resistor R23 connected to the inverting terminal of an operational amplifier 86 and a capacitor C10 connected between the inverting terminal and the output terminal of the operational amplifier. The output "Sweep" of the operational amplifier provides a linear time-base voltage varying from a minimum voltage of say 5V to a maximum voltage of say 12V under the control of comparator 50. The comparator 50 comprises an operational amplifier 88 having its inverting terminal connected to source V+ through resistors R24 and R25 and its inverting terminal connected to the junction of resistors R26 and R27 which are connected in series with a diode D10 between the "sweep" output of the operational amplifier 86 and ground. A resistor R28 is connected between the non-inverting terminal and the output terminal of the operational amplifier 88 for controlling the gain thereof in known manner. The output of operational amplifier 88 is connected to the non-inverting terminal of the operational amplifier 86 through a coupling resistor R29. The "sweep" output of the ramp generator is shown at V in FIG. 2 of the drawings but not on the same time scale as the other waveforms. The time lapse between $t_1$ and $t_2$ is about 0.7 sec and between $t_5$ and $t_6$ about 2 sec. The amplitudes of the echo signals at times $t_3$, $t_4$ and $t_5$ are shown at G, H and I in FIG. 2 of the drawings. At the beginning of the measurement cycle, the gain of the AGC amplifier 26 is low but it gradually increases until at time $t_5$ the retinal echo exceeds the threshold set by comparator 34. At such time, the "Stop" input of gate 70 turns low and, if the other two inputs of gate 70 are also low (in the time slots generated by the gate width generator 38 and the R.E.T. gate width generator 44), the output T of gate 70 turns high.

The output T of gate 70 is applied to a display duration monostable circuit comprising a CMOS NOR gate 90 and inverter 92. The first input of gate 90 is connected to the output of gate 70 and its second input is connected to the output of the inverter 92. The output of the gate 90 is connected to the input of inverter 92 through a capacitor C11. A positive potential source V+ is also connected to the input of inverter 92 through resistor R30. A protective diode D11 is connected across resistor R30 to protect the inverter against overvoltage. The output of the monostable is shown at U in FIG. 2 of the drawings. The output signal U is applied to the "Display enable" terminal of the counter and display 12 to stop the counter and show the axial length of the eye for a period of time determined by the time constant of resistor R30 and capacitor C11. The output U of the inverter 92 is applied to an inverter 94 which produces the output "Display enable" which is applied to the slow clock 14 to enable the slow clock. The output "Display enable" is also applied to the inverting terminal of operational amplifier 86 through diode D12 to reset the gain sweep ramp voltage generator 48.

It will be seen from the above description that the counter 12 will be stopped and the display turned on only if (1) the output of the automatic gain amplifier 26 exceeds the threshold set by the comparator 34 and if (2) this occurs during the short time interval that the gate circuit 32 (or CMOS NOR gate 70) is enabled by the R.E.T. gate width generator 44 as indicated by waveform R in FIG. 2 of the drawings. If the beam is off-axis, the retinal echo will not have enough amplitude to stop the counter (which is then automatically reset on the next pulse transmitted). As a result, the echo-oculometer in accordance with the present invention behaves as if the beam directivity was much greater than it actually is. More importantly, mistriggering by echoes from structures behind the retina is eliminated by the latching circuit 42 which prevents the R.E.T. gate width generator 44 from being retriggered by echoes from structures behind the retina after it has been triggered by the retinal echo pulses. It is also important to note that the signal E appearing at the output of fixed gain amplifier 24 is amplified by an amount approximately 10 to 14 dB greater than the maximum gain of the AGC amplifier 26 to make sure that the first echo signal exceeding the threshold of the comparator 30 is positively a retinal echo signal and not an echo signal originating from a structure behind the retina as would happen if the retinal echo was of lower amplitude than the threshold set by the comparator 30.

Although the invention has been disclosed with reference to a workable embodiment shown in FIG. 3 of the drawings, it is to be understood that other detailed circuit diagrams could be used for the blocks of FIG. 1 and that the invention is not limited to such detailed circuit diagrams.

The embodiments of the invention in which an exclusive property or privilege is claimed are defined as follows:

1. An apparatus for measuring the axial length of an eye comprising:
 (a) a transducer adapted to transmit repetitive ultrasonic pulses along the ocular axis of the eye of a patient and to receive echo pulses reflected from the retina of the eye;
 (b) a fixed gain amplifier connected to said transducer for amplifying said reflected echo pulses;
 (c) an automatic gain controlled amplifier also connected to said transducer for amplifying said reflected echo pulses;
 (d) control means coupled to said automatic gain controlled amplifier for gradually increasing the gain of the amplifier during a measurement cycle;
 (e) first and second gate circuits coupled to the output of the fixed and automatic gain controlled amplifier, respectively, and adapted to pass logic signals triggered by retinal echo pulses exceeding first and second predetermined thresholds;
 (f) a digital counter connected to the second gate circuit and adapted to display the axial length of the eye as a function of the distance travelled by the retinal echo pulses;
 (g) a slow clock;
 (h) a gate delay initiated by said slow clock;
 (i) a gate width generator connected to said gate delay for generating a time slot during which echo pulses originating from the posterior wall of the eye can be received;
 (j) a latching circuit responsive to said gate delay for enabling said first gate circuit to pass logic signals triggered by echo pulses from the posterior wall of the eye exceeding said first threshold;
 (k) a retinal echo triggered gate width generator interconnecting said first and second gate circuits and responsive to said first gate circuit for enabling said second gate circuit to pass logic signals triggered by retinal echo pulses exceeding said second threshold in the time slot generated by said gate width generator, the output of said retinal echo triggered gate width generator being also connected to the latching circuit for blocking the first gate circuit immediately after receipt of the first logic signal triggered by a retinal echo pulse, thereby preventing mistriggering of the retinal echo triggered gate width generator by echoes originating from structures behind the retina.

2. An echo-oculometer as defined in claim 1, wherein said control means includes a slow ramp generator adapted to generate a ramp voltage which is applied to the variable gain amplifier in such a manner that the gain of the amplifier varies from a minimum at the start of the measurement cycle to a preset maximum gain at the end of the measurement cycle.

3. the gain of said fixed gain amplifier is approximately 10 to 14 dB greater than the maximum gain of the automatic gain controlled amplifier to make sure that any retinal echo signal will exceed the first threshold thereby preventing mistriggering of the retinal echo triggered gate width generator circuit by echoes originating from structures behind the retina.

4. An echo-oculometer as defined in claim 1, further comprising a fast clock adapted to generate a signal of a frequency which is numerically proportional to the average velocity of ultrasound in the eye and provides a time base for the counter.

5. An echo-oculometer as defined in claim 4, further comprising a pulser responsive to said slow clock and connected to said transducer for applying sharp high voltage spikes to said transducer to shock excite the transducer to produce said ultrasonic pulses, and wherein the slow clock is responsive to said fast clock for controlling the rate of said repetitive ultrasonic pulses.

6. An echo-oculometer as defined in claim 5, further comprising a pulser delay interconnecting said slow clock to said pulser for controlling the time interval between the time the ultrasonic pulses are generated and the time the counter starts counting.

7. An echo-oculometer as defined in claim 1, further comprising a display duration circuit interconnecting said second gate circuit and said digital counter and display for allowing display of the axial length of the eye for a predetermined interval.

8. An echo-oculometer as defined in claim 1, further comprising comparators interconnecting said fixed gain and automatic gain controlled amplifiers to said first and second gate circuits, respectively, for setting up said first and second thresholds.

* * * * *

UNITED STATES PATENT AND TRADEMARK OFFICE
CERTIFICATE OF CORRECTION

PATENT NO. : 4,261,367
DATED : April 14, 1981
INVENTOR(S) : MANFRED FREESE

It is certified that error appears in the above—identified patent and that said Letters Patent is hereby corrected as shown below:

Claim 3, line 1, insert

-- An echo-oculometer as defined in claim 2, wherein --

Signed and Sealed this

Eighteenth Day of August 1981

[SEAL]

*Attest:*

GERALD J. MOSSINGHOFF

*Attesting Officer*     *Commissioner of Patents and Trademarks*